(12) United States Patent
Wang et al.

(10) Patent No.: US 9,366,634 B2
(45) Date of Patent: Jun. 14, 2016

(54) SUBSTRATE ENHANCED LASER-INDUCED BREAKDOWN SPECTROSCOPY (LIBS) APPARATUS

(71) Applicants: Sean Xiaolu Wang, Wilmington, DE (US); Qun Li, Newark, DE (US)

(72) Inventors: Sean Xiaolu Wang, Wilmington, DE (US); Qun Li, Newark, DE (US)

(73) Assignee: BWT Property, Inc., Newark, DE (US)

( * ) Notice: Subject to any disclaimer, the term of this patent is extended or adjusted under 35 U.S.C. 154(b) by 0 days.

(21) Appl. No.: 14/918,839

(22) Filed: Oct. 21, 2015

(65) Prior Publication Data
US 2016/0116416 A1    Apr. 28, 2016

Related U.S. Application Data

(60) Provisional application No. 62/067,263, filed on Oct. 22, 2014, provisional application No. 62/083,482, filed on Nov. 24, 2014.

(51) Int. Cl.
*G01J 3/30* (2006.01)
*G01N 21/71* (2006.01)
*G01N 33/28* (2006.01)

(52) U.S. Cl.
CPC .......... *G01N 21/718* (2013.01); *G01N 33/2888* (2013.01); *G01N 2201/06113* (2013.01)

(58) Field of Classification Search
CPC ..... G01N 21/718; G01N 33/2888; G01J 3/02; G01J 3/4406; G01J 3/6458
USPC .................................................. 356/300–445
See application file for complete search history.

(56) References Cited

U.S. PATENT DOCUMENTS

| | | | |
|---|---|---|---|
| 7,394,537 B1 | 7/2008 | Lindfors et al. | |
| 7,999,928 B2 | 8/2011 | Beckstead et al. | |
| 2004/0002162 A1* | 1/2004 | Leugers ................. | G01N 21/03 436/171 |
| 2012/0033212 A1 | 2/2012 | Barefield, II | |
| 2013/0016349 A1* | 1/2013 | Effenberger, Jr. ......... | G01J 3/18 356/318 |
| 2014/0038091 A1* | 2/2014 | Grimbergen .............. | G03F 1/80 430/5 |

* cited by examiner

*Primary Examiner* — Abdullah Nur

(57) ABSTRACT

This invention discloses a substrate enhanced laser-induced breakdown spectroscopy (LIBS) apparatus for liquid analysis. The LIBS apparatus comprises a pulsed laser for producing a laser beam, a substrate made of a material having a high absorption coefficient at the laser wavelength for receiving the liquid sample, an optical lens or mirror for focusing the laser beam onto the liquid sample to produce a plasma emission, and a spectrometer for measuring the optical spectrum of the plasma emission. When the thickness of the liquid sample reaches an optimum value, the plasma emission from the liquid sample is enhanced by the substrate to produce a strong LIBS signal for spectral analysis.

13 Claims, 6 Drawing Sheets

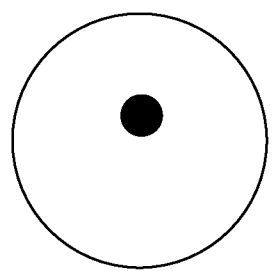
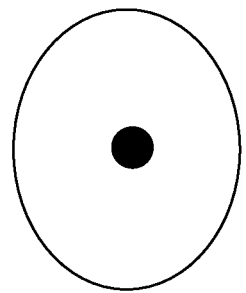
Fig. 7a    Fig. 7b
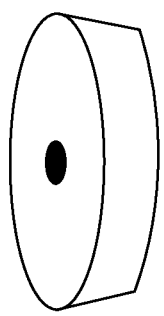
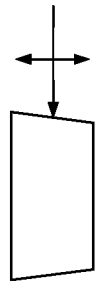
Fig. 7c

SUBSTRATE ENHANCED LASER-INDUCED BREAKDOWN SPECTROSCOPY (LIBS) APPARATUS

REFERENCE TO RELATED APPLICATION

This application claims inventions which were disclosed in Provisional Patent Application No. 62/067,263, filed Oct. 22, 2014, entitled "SUBSTRATE ENHANCED LASER-INDUCED BREAKDOWN SPECTROSCOPY (LIBS) APPARATUS" and Provisional Patent Application No. 62/083,482, filed Nov. 24, 2014, entitled "LASER-INDUCED BREAKDOWN SPECTROSCOPY (LIBS) APPARATUS FOR LIQUID ANALYSIS". The benefit under 35 USC §119(e) of the above mentioned United States Provisional Applications is hereby claimed, and the aforementioned applications are hereby incorporated herein by reference.

FIELD OF THE INVENTION

This invention generally relates to a laser-induced breakdown spectroscopy (LIBS) apparatus, and more specifically to a substrate enhanced laser-induced breakdown spectroscopy (LIBS) apparatus.

BACKGROUND

Laser-induced breakdown spectroscopy (LIBS) is a type of atomic emission spectroscopy which uses a highly energetic laser pulse as the excitation source. The laser pulse generates a high temperature micro-plasma on the surface of the sample. After this excitation, light that is characteristic of the elemental composition of the sample is emitted and analyzed within a spectrometer. LIBS has become a very popular analytical method in view of some of its unique features such as applicability to any type of sample, practically no sample preparation, remote sensing capability, and speed of analysis.

Many applications require performing LIBS analysis on liquid samples. One example is identification of metallic wear debris from machinery lubricant, which allows the machinery maintainer to assess the health of the engine or gearbox and identify specific component damage. However, studies have shown that plasma emission is quenched in a liquid sample such as the machinery lubricant, resulting in a reduction in both plasma light intensity and the length of time during which plasma emission can be observed. In addition, some liquid sample is highly transparent to certain laser wavelengths, which raises the threshold of the required laser pulse energy to produce plasma emission. There thus exists a need for a more efficient way to produce and measure laser induced plasma emission in liquid samples.

SUMMARY OF THE INVENTION

It is thus the goal of the present invention to provide a substrate enhanced laser-induced breakdown spectroscopy (LIBS) apparatus for liquid analysis. The LIBS apparatus comprises a pulsed laser for producing a laser beam, a substrate made of a material having a high absorption coefficient at the laser wavelength for receiving the liquid sample, an optical lens or mirror for focusing the laser beam onto the liquid sample to produce a plasma emission, and a spectrometer for measuring the optical spectrum of the plasma emission. When the thickness of the liquid sample reaches an optimum value, the plasma emission from the liquid sample is enhanced by the substrate to produce a strong LIBS signal for spectral analysis.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIGS. 7a-c illustrate different shaped substrate for laser focusing control.

Figure 1:
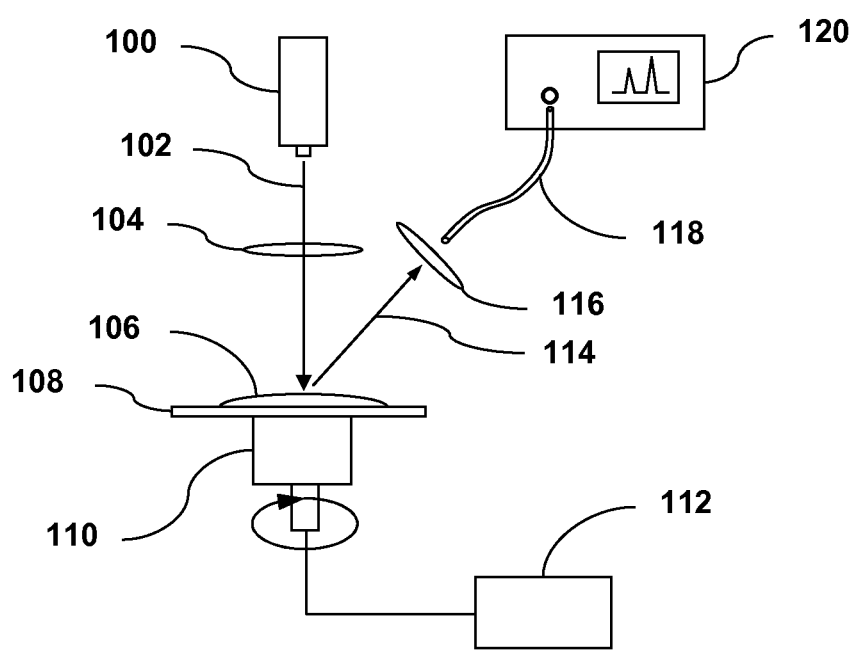
FIG. 1 illustrates a first exemplary embodiment of the substrate enhanced laser-induced breakdown spectroscopy (LIBS) apparatus for liquid analysis.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a substrate enhanced laser-induced breakdown spectroscopy (LIBS) apparatus. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

A first exemplary embodiment of the substrate enhanced laser-induced breakdown spectroscopy (LIBS) apparatus is shown in FIG. 1, which is optimized for liquid sample analysis. The LIBS apparatus comprises a pulsed laser 100 as the excitation light source. The pulsed laser 100 is a passively or actively Q-switched laser, or a mode-locked laser, or more preferably a passively Q-switched diode pumped solid state (DPSS) laser. The pulsed laser 100 preferably has a high repetition rate of >100 Hz, more preferably >1000 Hz (1 KHz) for producing a train of laser pulses. A substrate 108 made of a material (e.g. a metal) having a high absorption coefficient at the laser wavelength is configured to receive the liquid sample 106. The laser beam 102 from the pulsed laser 100 is focused by an objective lens 104 onto the liquid sample 106. The laser pulse produces a plasma emission, i.e. LIBS signal 114 from the liquid sample 106, which is collected by a focusing lens 116 to be focused into a light guide 118, such as an optical fiber or fiber bundle. The light guide 118 then delivers the LIBS signal 114 into an optical spectrometer device 120 for spectral analysis. In a slight variation of the LIBS apparatus, the objective lens 104 and the focusing lens 116 may be replaced with other types of optical focusing elements, such as concave mirrors, to avoid chromatic aberration of the optical lenses.

By adjusting the integration time of the spectrometer device 120 to cover a plurality of periods of the laser pulse train, the spectrometer device 120 can integrate the LIBS signal produced by a plurality of laser pulses. Hence the intensity of the obtained LIBS spectrum can be greatly improved to increase the signal-to-noise ratio (SNR) of the obtained LIBS spectrum. This unique feature of the high repetition rate laser based LIBS apparatus allows it to measure trace elements with very low concentration, hence reducing the limit of detection (LOD) of the LIBS apparatus. The increased signal intensity also lessens the sensitivity requirement for the optical spectrometer device 120. In addition, the energy of individual pulses in the laser pulse train can be reduced in comparison to conventional single shot or low repetition rate laser based LIBS apparatus to obtain the same signal level. Hence the laser pulse is less invasive to the sample. Since the obtained LIBS spectrum is the spectrum of a plurality of micro-plasma produced by a plurality of laser pulses, the influence of pulse to pulse variation of the laser is also minimized.

Referring back to FIG. 1, the substrate 108 is mounted on a chuck 110, which is rotated to cause the substrate 108 to spin at a high speed in order to spread the liquid sample 106 by centrifugal force. Rotation is continued while the liquid spins off the edges of the substrate 108, until the desired thickness is achieved. The rotational speed and acceleration of the chuck 110 is controlled by a controller 112 so as to control the final thickness of the liquid sample 106. When the thickness of the liquid sample 106 is controlled to reach an optimum value (e.g. several microns ($\mu$m) to a few hundreds of microns ($\mu$m)), the high absorption coefficient of the substrate 108 to the laser beam helps to enhance the plasma emission from the liquid sample 106 and produce a strong LIBS signal for spectral analysis. The enhancement can be several orders of magnitude depending on the physical properties of the liquid and the substrate material. When the liquid sample 106 is thin (e.g. several microns ($\mu$m)), the measured LIBS spectrum contains the spectral lines of both the liquid and the substrate material. This indicates that the laser pulse produces plasma emission from both the liquid sample 106 and the substrate 108. When the liquid sample 106 is relatively thicker (e.g. a few hundreds of microns ($\mu$m)), the measured LIBS spectrum contains only the spectral lines of the liquid. So at this thickness, the plasma emission from the liquid sample 106 is enhanced and the plasma emission from the substrate 108 is minimized to a negligible level. In cases where the liquid sample 106 is too thick, the substrate 108 could not provide enhancement to the plasma emission of the liquid. The LIBS signal will become very weak and even not observable. The variation of the relative intensity of the LIBS spectral lines of the liquid and the substrate may be utilized as a feedback to the controller 112 for more precisely controlling the thickness of the liquid sample 106.

In a slight variation of the present embodiment, a thickness sensor, such as a laser interferometer (not shown) is employed to measure the thickness of the liquid on the substrate. The measurement result from the thickness sensor may be used as a feedback signal to the controller 112 for more precise control of the thickness of the liquid.

In another variation of the present embodiment, the laser beam 102 is focused by the objective lens 104 into the liquid sample 106 to produce a plasma emission from a focal point inside the liquid sample 106. The distance between the focal point and the substrate 108 is controlled such that the plasma emission from the liquid sample 106 is enhanced by the substrate 108. Similarly, when the distance between the focal point and the substrate 108 reaches an optimum value, the plasma emission from the liquid sample 106 is enhanced and the plasma emission from the substrate 108 is minimized.

The same concept can be applied to gas analysis as well. The laser beam from a pulsed laser light source is focused by an objective lens to a focal point in front of a substrate, which is immersed in the gas to be analyzed. The substrate is made of metal or any material having high absorption coefficient to the laser beam. The laser beam produces plasma emission from the gas at the focal point. The optical spectrum of the plasma emission is analyzed by a spectrometer device to determine the content and concentration of gas. By controlling the distance between the focal point and the substrate, the plasma emission from the gas is enhanced by the substrate. When the distance between the focal point and the substrate reaches an optimum value, the plasma emission from the gas is enhanced and the plasma emission from the substrate is minimized to reduce its interference.

Figure 2A:
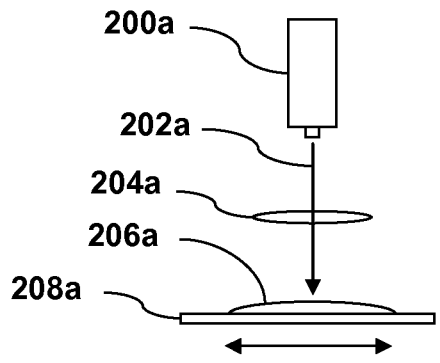
FIGS. 2a-2d illustrate various methods for controlling the thickness of the liquid sample on the substrate.
Figure 2B:
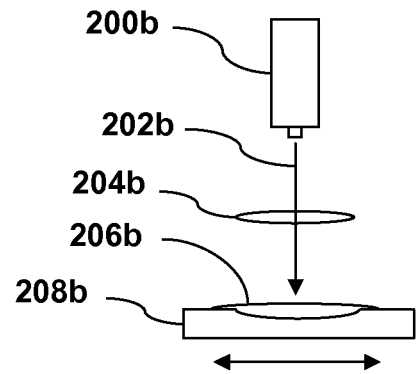
Figure 2C:
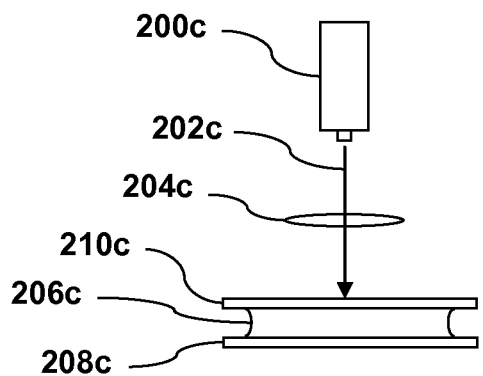
Figure 2D:
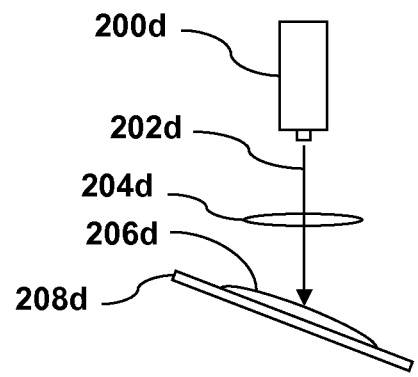

There are numerous ways of controlling the thickness of the liquid sample on the substrate. FIG. 2a-d shows a few examples. In FIG. 2a, the volume of the liquid sample 206a is controlled such that the gravity of the liquid sample 206a and the surface tension between the liquid and the substrate 208a will automatically set the liquid sample 206a to a desired thickness. In addition, the substrate 208a and the liquid sample 206a may be moved laterally in relative to the laser beam 202a until the laser beam 202a strikes the region of the liquid sample having the optimum thickness. Alternatively, the pulsed laser 200a and/or the objective lens 204a may be moved laterally in relative to the liquid sample 206a and the substrate 208a to search for the optimum sample thickness. The thickness of the liquid sample can be further controlled by controlling the surface energy of the substrate material. In FIG. 2b, the substrate 208b is made with a well for receiving the liquid sample 206b. The depth of the well is pre-defined to control the thickness of the liquid sample 206b in the well. In a similar way as shown in FIG. 2a, the pulsed laser 200b, the objective lens 204b, and the substrate 208b can be moved laterally in relative to each other to scan the laser beam 202b over the sample until the laser beam 202b strikes the region of the liquid sample having the optimum thickness. In FIG. 2c, the liquid sample 206c is sandwiched between a transparent cover 210c and a substrate 208c. The thickness of the liquid sample 206c is controlled by adjusting the distance between the transparent cover 210c and the substrate 208c. The laser beam 202c from the pulsed laser 200c is focused by the objective lens 204c into the liquid sample 206c to produce a plasma emission inside the liquid sample 206c. The plasma emission is enhanced by the substrate 208c to produce a strong LIBS signal for spectral analysis. Here the transparent cover 210c can be part or an extension of the optical system for focusing the laser beam 202c. For example, it can be an extendable/retractable optical window which covers the objective lens 204c. On one hand, it protects the objective lens 204c from contamination. On the other hand, it can be moved towards the surface of the liquid sample 206c for controlling the thickness of the liquid sample 206c. Yet as another slight variation of FIG. 2c, the liquid sample 206c can be confined within a rectangular tube which has a transparent wall 210c, a substrate wall 208c, and another two vertical walls which are not shown in the figure. The thickness of the liquid sample 206c is predefined by the distance between the transparent wall 210c and the substrate wall 208c. The laser beam 202c from the pulsed laser 200c is focused by the objective lens 204c into the liquid sample 206c to produce a plasma emission inside the liquid sample 206c. The plasma emission is enhanced by the substrate wall 208c to produce a strong LIBS signal for spectral analysis. In FIG. 2d, the substrate 208d is tilted. The thickness of the liquid sample 206d will vary at different tilt angles due to gravity force. In addition, the tilt angle sets the incident angle of the laser beam 202d into the liquid sample 206d, which also determines the thickness of the liquid sample 206d under analysis. Thus by controlling the tilt angle of the substrate 208d and other parameters such as the surface roughness of the substrate 208d, the volume and viscosity of the liquid sample 206d, the thickness of the liquid sample 206d can be precisely controlled. In a similar way as shown in FIG. 2a, the laser beam 202d from the pulsed laser 200d is focused by the objective lens 204d onto the liquid sample 206d to produce a plasma emission. The plasma emission is enhanced by the substrate 208d to produce a strong LIBS signal.

Figure 3A:
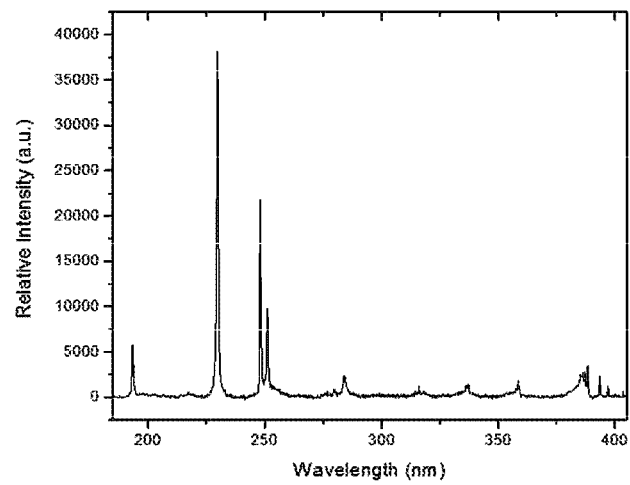
FIGS. 3a-3b are the measured LIBS spectra of an engine oil sample, which is deposited on top of an aluminum substrate.
Figure 3B:
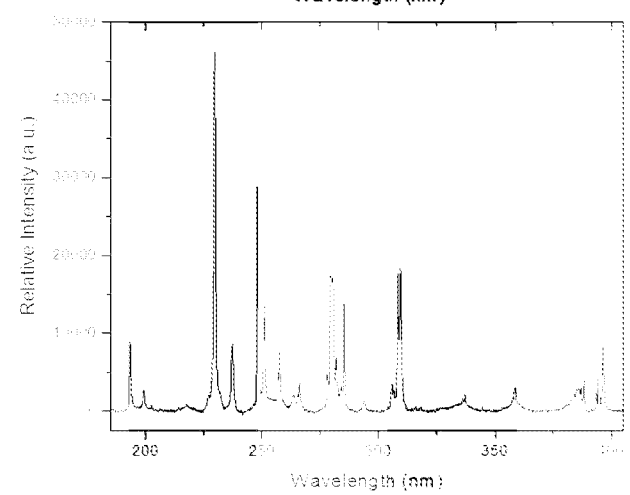
Figure 3C:
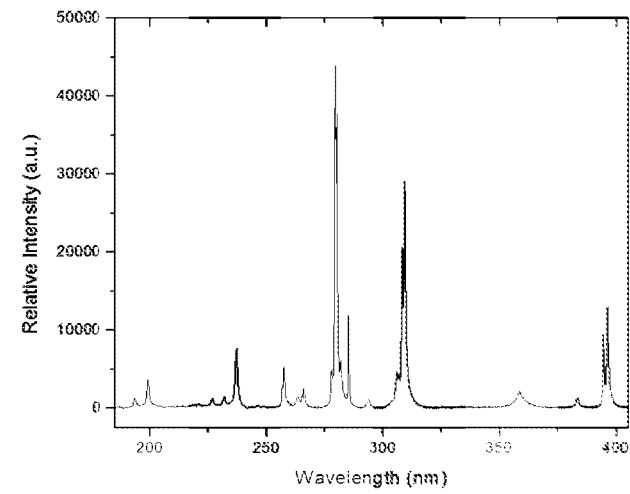
FIG. 3c is the LIBS spectrum of the aluminum substrate for comparison.

As one example, the LIBS spectrum of an engine oil sample is measured with the substrate enhanced LIBS apparatus. In this example, the laser light source is a passively Q-switched Nd:YAG laser emitting at a wavelength of 1064 nm. The laser pulse energy is 20 µJ with a pulse width of 0.5 ns. The repetition rate of the laser pulse is 5 kHz. The LIBS spectrum is measured with a CCD spectrometer covering a wavelength range of 180-450 nm. The engine oil sample is nearly transparent at the laser wavelength. So the laser energy is poorly absorbed by the sample, causing the laser to produce no plasma emission when it hits the sample directly. However, when the engine oil sample is deposited on an aluminum substrate and the thickness of the oil layer is controlled to be several micron (µm) to a few hundreds of micron (µm), the high absorption coefficient of the aluminum substrate to the laser beam helps to enhance the plasma emission from the engine oil and a strong LIBS signal is observed. FIG. 3a and FIG. 3b show the measured LIBS spectra of the engine oil sample at two thicknesses. One is around 100 µm and the other is around 10 µm. In both cases, the plasma emission of the engine oil is enhanced by more than two orders of magnitude by the aluminum substrate. When the oil layer is relatively thin, the measured LIBS spectrum contains the spectral lines of both the engine oil sample and the aluminum substrate as shown in FIG. 3b (the LIBS spectrum of the aluminum substrate is shown in FIG. 3c for comparison). This indicates that the laser pulse produces plasma emission from both the engine oil and the aluminum substrate. While at an oil thickness of around 100 µm, the measured LIBS spectrum contains only the spectral lines of the engine oil as shown in FIG. 3a. So at this thickness, the plasma emission from the engine oil is enhanced and the plasma emission from the aluminum substrate is minimized to a negligible level.

Figure 4:
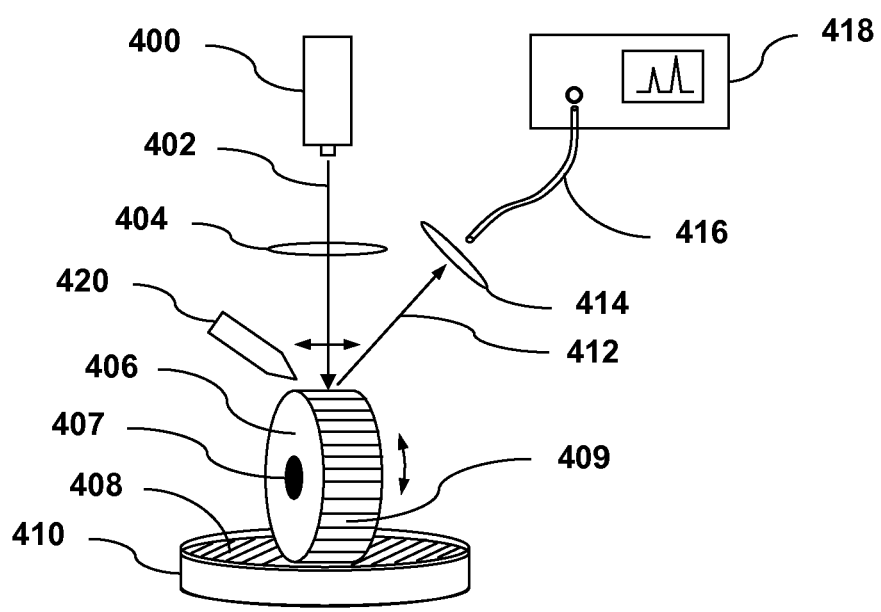
FIG. 4 illustrates a second exemplary embodiment of the substrate enhanced laser-induced breakdown spectroscopy (LIBS) apparatus for liquid analysis.

FIG. 4 illustrates a second exemplary embodiment of the substrate enhanced laser-induced breakdown spectroscopy (LIBS) apparatus. The LIBS apparatus comprises a pulsed laser 400 as the excitation light source. A wheel shaped substrate 406 is configured to receive the liquid sample 408 from a container 410. The substrate 406 is made of metal or any kind of material having a high absorption coefficient at the laser wavelength. The wheel shaped substrate 406 rotates around its axis 407 at a controlled speed. When it dips into the container 410, a small portion of the liquid sample 408 adheres to its side surface. The liquid spreads on the side surface of the wheel shaped substrate 406 as it rotates and forms a thin liquid film 409. By controlling the rotating speed of the wheel shaped substrate 406 and other parameters such as the material, temperature, and surface condition of the substrate with one or more controllers (not shown), the thickness of the liquid film 409 can be precisely controlled. The laser beam 402 from the pulsed laser 400 is focused by an objective lens 404 onto the liquid film 409. The laser pulse produces a plasma emission, i.e. LIBS signal 412 from the liquid film 409, which is collected by a focusing lens 414 to be focused into a light guide 416, such as an optical fiber or fiber bundle. The light guide 416 then delivers the LIBS signal 412 into an optical spectrometer device 418 for spectral analysis. In this exemplary embodiment, the laser beam 402 is scanned in a direction parallel to the axis of the wheel shaped substrate 406 to repeatedly sample a fresh surface of the liquid film 409. Combined with the high repetition rate of the pulsed laser 400, this scanning action helps to produce a more stable plasma emission from the liquid film 409. Scanning of the laser beam can be achieved, for example, by moving the objective lens 404 with a linear translation stage or a vibrator (not shown) or by using a galvanometer mirror or MEMS mirror. In a slight variation of the LIBS apparatus, an electrode 420 is provided to produce a high voltage electrical field between the electrode 420 and the metal substrate 406. The electrical field helps to enhance the intensity of the plasma emission, improve its stability, and prolong its duration to improve the quality of the LIBS signal.

According to another aspect of the present invention, the thickness of the liquid film 409 on the substrate 406 may be utilized to monitor the viscosity of the liquid 408. Other conditions set, the amount of liquid adhered to the surface of the substrate are proportional to the viscosity of the liquid. So by controlling the rotating speed and the temperature of the substrate, the thickness of the liquid film will be proportional to the viscosity of the liquid. As disclosed above, the relative intensity of the LIBS spectral lines of the liquid and the substrate varies with the thickness of the liquid film. This variation may be utilized to estimate the thickness of the liquid film, hence the viscosity of the liquid. Alternatively, an independent sensor, such as an optical interferometer device may be employed to monitor the thickness of the liquid film.

Figure 5:
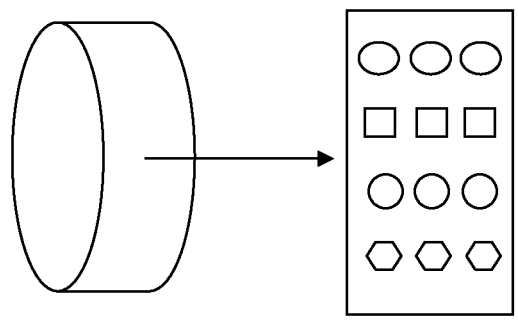
FIG. 5 illustrates a substrate with microstructures for receiving the liquid sample.
Figure 6A:
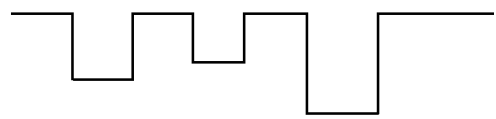
FIGS. 6a-e illustrate various depth profiles of the microstructures shown in FIG. 5.
Figure 6B:
Figure 6C:
Figure 6D:
Figure 6E:
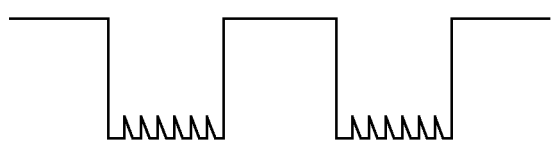

The side surface of the wheel shaped substrate may be manufactured with different shaped microstructures as shown in FIG. 5 to further enhance the quality of the LIBS signal. The microstructures can be either protrusions or wells whose depth profiles are shown in FIGS. 6a-e as a few examples. In FIG. 6a, the side surface of the substrate comprises a plurality of wells for receiving the liquid sample. The depth of the well is pre-defined to control the thickness of the liquid in the well. As disclosed above, when the thickness of the liquid reaches an optimum value, the plasma emission from the liquid is enhanced by the substrate yet the plasma emission from the substrate is minimized. In this exemplary embodiment, the wells may have different depths. Thus when the laser beam is scanned across the side surface of the substrate, it will hit liquid samples with different thickness. A predefined sorting or other kinds of mathematical post-processing of the collected LIBS spectra is performed to select the LIBS spectrum with the best quality in terms of signal-to-noise ratio, interference from substrate, etc. In FIG. 6b, the side surface of the substrate comprises a plurality of wells which have narrowed bottleneck section near their opening. These wells help to confine the plasma emission of the liquid into a small space such that the intensity of the plasma emission is enhanced. In FIG. 6c, the wells have a sloped depth profile such that the thickness of the liquid varies gradually in the well. As the laser beam is scanned across the well, LIBS spectra at different liquid thickness will be collected and a similar sorting mechanism will be employed to select the LIBS spectrum with the best quality. In FIG. 6d, the side surface of the substrate comprises a plurality of micro-scaled protrusions. These micro-scaled protrusions help to enhance the electric field of the incident laser beam. As a result, the plasma emission from the liquid sample is also enhanced. In addition, the micro-scaled protrusions may also increase the localized electrical field which is produced by the electrode 420 in FIG. 4 for enhanced plasma emission. In FIG. 6e, the side surface of the substrate comprises wells with micro-scaled protrusions at the bottom of the well for both liquid thickness control and electric field enhancement.

LIBS measurement requires that the laser beam is precisely focused on the surface of the sample. In the exemplary embodiment of the present invention as shown in FIG. 4, laser focusing is achieved by controlling the distance from the objective lens 404 to the side surface of the wheel shaped substrate 406. FIGS. 7a-c show some alternative approaches for laser focusing control. In FIG. 7a, the wheel shaped substrate has an off-centered axis. As it rotates around the axis, the distance from its side surface to the objective lens (not shown) will vary. This distance variation ensures that the laser beam is focused on the surface of the liquid film at a specific position of the rotating substrate even though the thickness of the liquid film changes. In FIG. 7b, the wheel shaped substrate has an elliptical cross-section. Thus the distance from its side surface to the objective lens (not shown) will also vary as it rotates to ensure precise laser focusing at a specific position. In FIG. 7c, the substrate is shaped like a conical frustum instead of a cylinder. When the laser beam is scanned across its side surface, the laser beam will be focused at different depths to ensure precise laser focusing at a specific position. Under the approaches illustrated in FIGS. 7a-c with the combination of a high repetition rate laser, no close-loop focusing control is necessary. There are always good focused LIBS spectra available among all the spectra collected. The LIBS spectra with the best quality can be selected out of the whole spectrum set.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A substrate enhanced laser-induced breakdown spectroscopy (LIBS) apparatus for measuring the LIBS spectrum of a liquid sample, the LIBS apparatus comprising:
    a pulsed laser light source for producing a laser beam;
    a substrate made of a material having a high absorption coefficient to the laser beam for receiving the liquid sample;
    an optical focusing element for focusing the laser beam onto the liquid sample to produce a plasma emission from the liquid sample;
    a controller for controlling a thickness of the liquid sample on the substrate in such a way that the plasma emission from the liquid sample is enhanced by the substrate; and
    an optical spectrometer device for measuring an optical spectrum of the plasma emission.

2. The substrate enhanced laser-induced breakdown spectroscopy (LIBS) apparatus of claim 1, wherein the controller is configured to control the thickness of the liquid sample to an optimum value such that the laser beam produces minimized plasma emission from the substrate.

3. The substrate enhanced laser-induced breakdown spectroscopy (LIBS) apparatus of claim 1, wherein the pulsed laser light source has a high repetition rate of greater than 100 Hz.

4. The substrate enhanced laser-induced breakdown spectroscopy (LIBS) apparatus of claim 3, wherein the optical spectrometer device is set to an integration time which integrates the plasma emission produced by a plurality of laser pulses.

5. The substrate enhanced laser-induced breakdown spectroscopy (LIBS) apparatus of claim 1, wherein the pulsed laser light source is a passively Q-switched diode pumped solid state (DPSS) laser.

6. The substrate enhanced laser-induced breakdown spectroscopy (LIBS) apparatus of claim 1, wherein the substrate is a metal substrate.

7. The substrate enhanced laser-induced breakdown spectroscopy (LIBS) apparatus of claim 6, further comprising an electrode for producing an electrical field between the electrode and the substrate to enhance the plasma emission.

8. The substrate enhanced laser-induced breakdown spectroscopy (LIBS) apparatus of claim 1, wherein the substrate comprises microstructures in the form of protrusions and wells.

9. The substrate enhanced laser-induced breakdown spectroscopy (LIBS) apparatus of claim 1, further comprising a laser beam scanner for scanning the laser beam over a surface of the liquid sample.

10. A substrate enhanced laser-induced breakdown spectroscopy (LIBS) apparatus for measuring the LIBS spectrum of a liquid or gas sample, the LIBS apparatus comprising:
    a pulsed laser light source for producing a laser beam;
    a substrate made of a material having a high absorption coefficient to the laser beam for receiving the liquid or gas sample;
    an optical focusing element for focusing the laser beam into the liquid or gas sample to produce a plasma emission from a focal point inside the liquid or gas sample;
    a controller for controlling a distance between the focal point and the substrate in such a way that the plasma emission from the liquid or gas sample is enhanced by the substrate; and
    an optical spectrometer device for measuring an optical spectrum of the plasma emission.

11. The substrate enhanced laser-induced breakdown spectroscopy (LIBS) apparatus of claim 10, wherein the distance between the focal point and the substrate is controlled to an optimum value such that the laser beam produces minimized plasma emission from the substrate.

12. A method of using substrate enhanced laser-induced breakdown spectroscopy (LIBS) for measuring the LIBS spectrum of a liquid sample, the method comprising the steps of:
- providing a pulsed laser light source for producing a laser beam;
- providing a substrate made of a material having a high absorption coefficient to the laser beam for receiving the liquid sample;
- focusing the laser beam onto the liquid sample to produce a plasma emission from the liquid sample;
- controlling a thickness of the liquid sample on the substrate in such a way that the plasma emission from the liquid sample is enhanced by the substrate; and
- measuring an optical spectrum of the plasma emission.

13. The method of claim 12, wherein the thickness of the liquid sample is controlled to an optimum value such that the laser beam produces minimized plasma emission from the substrate.

\* \* \* \* \*